United States Patent
D'Aversa et al.

[11] Patent Number: 6,090,116
[45] Date of Patent: Jul. 18, 2000

[54] KNITTED SURGICAL MESH

[76] Inventors: Margaret M. D'Aversa, 33 Railroad Ave., Whitehouse Station, N.J. 08889; Robert Dougherty, 4996 Elderberry Dr., Reading, Pa. 19606

[21] Appl. No.: 09/269,980

[22] PCT Filed: Oct. 3, 1997

[86] PCT No.: PCT/US97/17987

§ 371 Date: Apr. 2, 1999

§ 102(e) Date: Apr. 2, 1999

[51] Int. Cl.[7] .................................................. A61B 17/04
[52] U.S. Cl. ............................................. 606/151; 54/243
[58] Field of Search ................................. 606/151; 57/243

[56] References Cited

U.S. PATENT DOCUMENTS

| | | | |
|---|---|---|---|
| 3,054,406 | 9/1962 | Usher | 606/151 |
| 4,347,847 | 9/1982 | Usher | 606/151 |
| 4,452,245 | 6/1984 | Usher | 606/151 |
| 4,655,221 | 4/1987 | Devereux | 606/151 |
| 5,292,328 | 3/1994 | Hain et al. | 606/151 |
| 5,569,273 | 10/1996 | Titone et al. | 606/151 |

*Primary Examiner*—Gary Jackson
*Attorney, Agent, or Firm*—Reed Smith Shaw & McClay LLP

[57] ABSTRACT

A knitted surgical mesh formed from a yarn. The knitted mesh has from 11 to 13 courses per inch and from 8 to 10 wales per inch, a flexibility of from 10 to 16 gfcm/cm, a burst strength greater than 175 pounds per square inch, and a pore size percentage greater than 37%.

10 Claims, 2 Drawing Sheets

KNITTED SURGICAL MESH

FIELD OF THE INVENTION

This invention relates to a textile material and, in particular, to a surgical mesh of knit construction fabricated from a polypropylene monofilament yarn.

BACKGROUND

Hernia repairs are among the more common surgical operations which may employ a mesh fabric prosthesis. Such mesh fabric prostheses are also used in other surgical procedures including the repair of anatomical defects of the abdominal wall, diaphragm, and chest wall, correction of defects in the genitourinary system, and repair of traumatically damaged organs such as the spleen, liver or kidney.

Mesh fabrics for use in connection with hernia repairs are disclosed in U.S. Pat. Nos. 5,292,328, 4,769,038 and 2,671,444. Knitted and woven fabrics constructed from a variety of synthetic fibers and the use of the fabrics in surgical repair are also discussed in U.S. Pat. Nos. 3,054,406; 3,124,136; 4,193,137; 4,347,847; 4,452,245; 4,520,821; 4,633,873; 4,652,264; 4,655,221; 4,838,884;. 5,002,551; and European Patent Application No. 334,046.

It is desirable for a surgical mesh fabric prosthesis to exhibit certain properties and characteristics. In particular, the mesh should have a burst strength sufficient to ensure that the mesh does not break or tear after insertion into a patient. The mesh should also have a pore size which allows tissue to penetrate or "grow through" the mesh, after the mesh has been inserted into a patient. In addition, the mesh should be constructed so as to maximize its flexibility, thereby facilitating the insertion of the mesh prosthesis into a patient during a surgical operation.

It is an object of the present invention to provided a knitted surgical mesh having a high burst strength and large pore size, which has a greater flexibility than known knitted surgical mesh fabrics.

These and other objects and advantages of the invention will become more fully apparent from the description and claims which follow or may be learned by the practice of the invention.

SUMMARY OF THE INVENTION

The present invention is directed to a knitted surgical mesh formed from a yarn. The knitted mesh has from 11 to 13 courses per inch and from 8 to 10 wales per inch, a flexibility of from 10 to 16 gfcm/cm, a burst strength greater than 175 pounds per square inch, and a pore size percentage greater than 37%.

BRIEF DESCRIPTION OF THE DRAWINGS

In order that the manner in which the above-recited and other advantages and objects of the invention are obtained and can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

DESCRIPTION OF THE PREFERRED EMBODIMENTS

Figure 1:
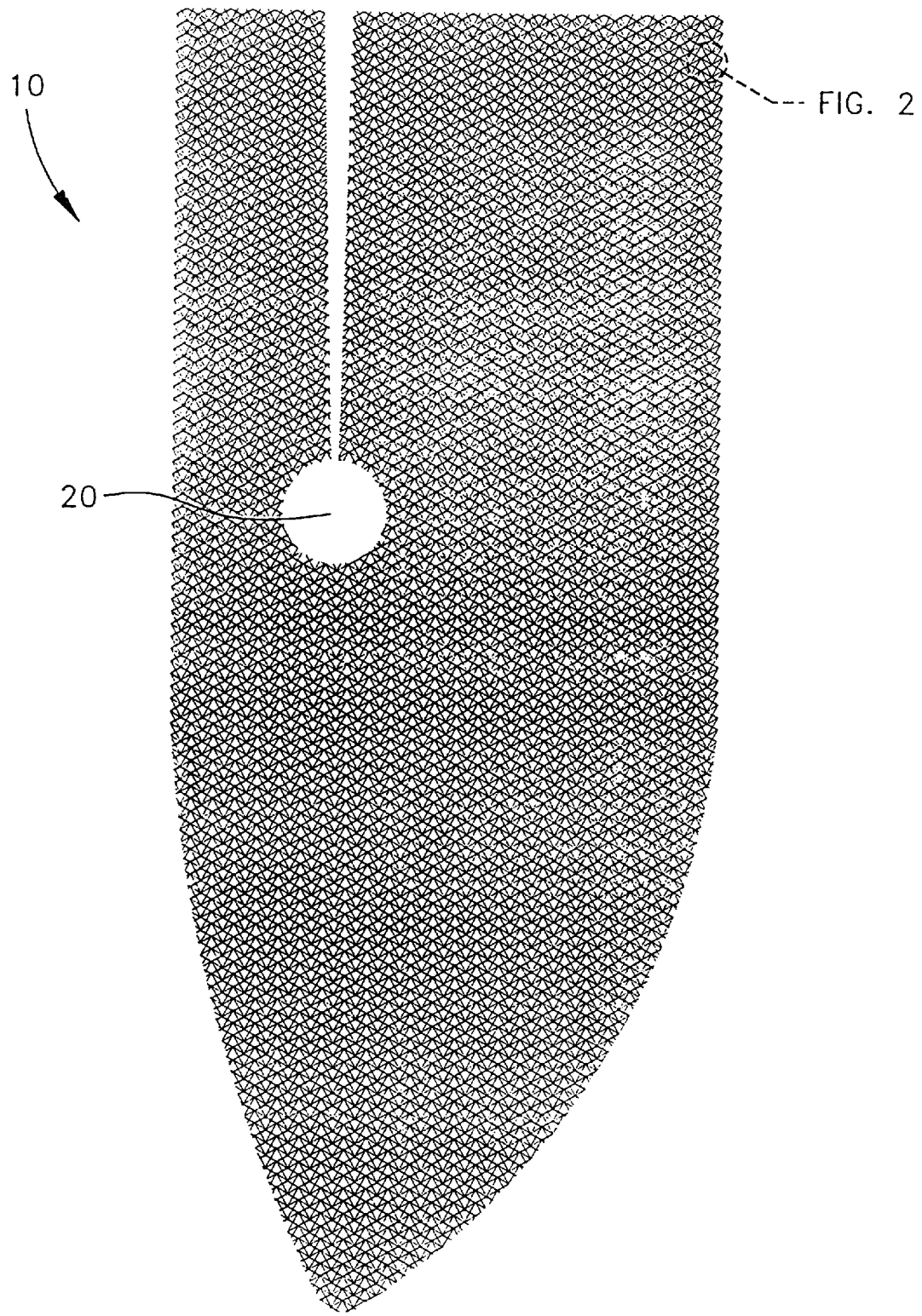
FIG. 1 is a diagram showing a knitted surgical mesh, in accordance with a preferred embodiment of the present invention.
Figure 2:
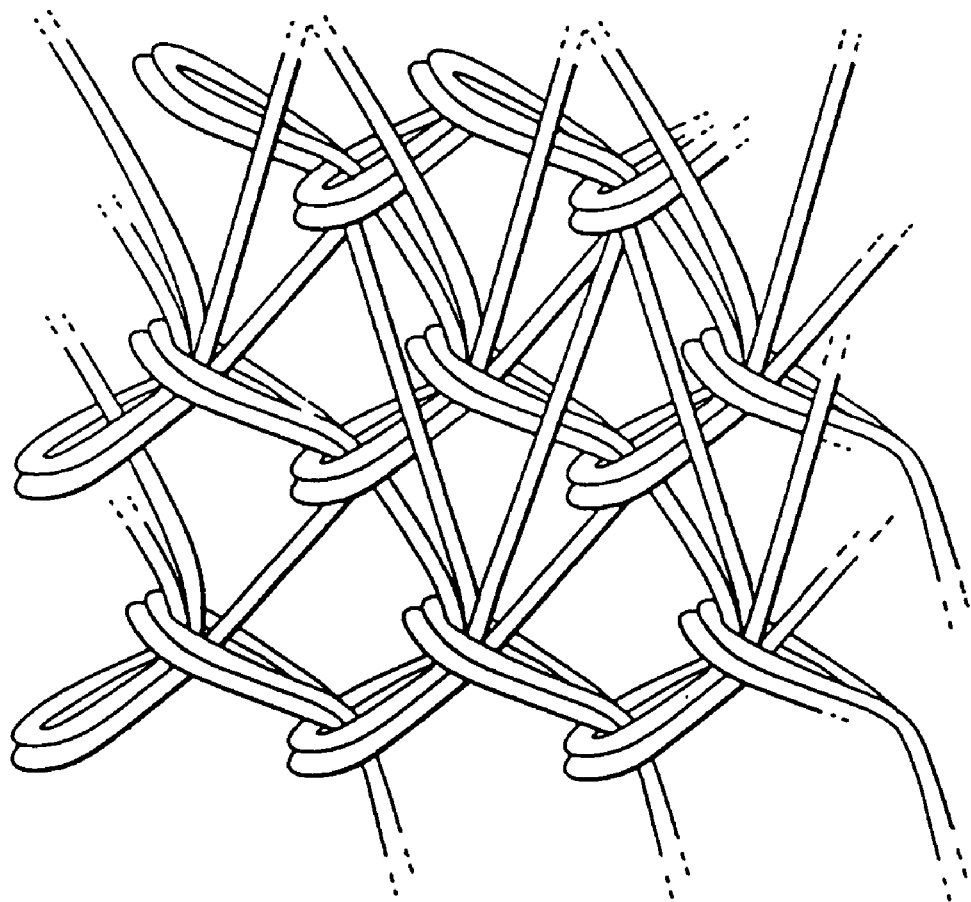
FIG. 2 is an enlarged view of a portion of the surgical mesh shown in FIG. 1.

The surgical mesh of this invention is preferably fabricated from a yarn which is already accepted for use as a suture material. In a preferred embodiment, the surgical mesh is fabricated from a monofilament yarn formed from a polypropylene resin, such as that disclosed in U.S. Pat. No. 4,911,165, entitled "Pliablized Polypropylene Surgical Filaments" and assigned to Ethicon, Inc., the contents of which is hereby incorporated in its entirety by reference. The preferred monofilament polypropylene yarn used has a denier of from about 30 to 300, and more preferably a denier of about 141. Alternatively, a multifilament yarn, such as a multifilament polypropylene yarn may be used to fabricate a surgical mesh in accordance with the present invention. In still further alternate embodiments, the yarn used to form the mesh may be formed from silk, linen, cotton, nylon, polyester (i.e., polyethelene terathalate, polybutulene terathalate, and mixtures thereof), polyethylene, stainless steel, hydrolytic polymers, such as those which may derived from lactone monomers, including but not limited to glycolide and lactide (including acid forms thereof), 1,4 dioxin, trimethylene carbonate, Δ-valero lactone, ε-caprolactone, 1,4 dioxepan-2-1, 1,5 dioxepan-2-1, and alkyl substituted equivalents of these compounds, as well as the cyclic dimers of these compounds.

The surgical mesh of this invention is preferably fabricated from a 141 denier monofilament polypropylene yarn by employing known and conventional warp knitting apparatus and techniques, such as the tricot and Raschel knitting machines and procedures described in "Warp Knitting Production" by Dr. S. Raz, Melliand Textilberichte GmbH, Rohrbacher Str. 76, D-6900 Heidelberg, Germany (1987), the contents of which are incorporated by reference herein. As is well known in the art of warp knitting, the number of courses and wales per inch in a knitted material is affected by a number of machine operating variables such as the rate at which the fabric is drawn away from the needles, the number of needles per inch, the amount of tension applied to the warp yarns and other variables after the fabric leaves the machine, e.g., the heat setting conditions. In the preferred embodiment of the present invention, the preferred polypropylene monofilament yarn described above is warp knitted, preferably tricot knitted on a 2 bar set-up, in accordance with the parameters set forth in Table I below:

TABLE I

| Courses per Inch | Wales per Inch | Back Bar | Front Bar |
| --- | --- | --- | --- |
| 11–13 | 8–10 | 2/3<br>1/0 | 1/2<br>1/0 |

Following knitting, the mesh is cleaned or scoured, and thereafter annealed to stabilize the fabric. For the latter operation, the mesh can be secured to a tenter frame which maintains the mesh at a predetermined width, the frame then being passed through an elongate heating zone at a temperature of from about 100° to about 160° C., preferably at a temperature of from about 120° to about 150° C., at a rate providing a dwell time of from about 1 to about 60 minutes and preferably from about 5 to about 25 minutes. Following heat setting, the mesh is cut to size, packaged and sterilized.

The mesh can be cut to any desired configuration, e.g., a square or rectangular shape, of appropriate dimensions. A preferred configuration 10 having a key-hole opening 20 is shown in FIG. 1. An ultrasonic slitter may be employed to cut the mesh, various types of which are commercially available. Unlike the result one obtains when cutting with a blade, i.e., frayed yarn ends, or when the yarn ends are heat-sealed, i.e., bead-like formations, cutting the mesh to size with an ultrasonic cutter avoids both frayed and beaded ends.

The polypropylene monofilament knitted mesh fabricated as described above exhibits high flexibility. Depending on the yarn used to form the mesh, a mesh formed in accordance with Table I above preferably has a flexibility of about 10 to 16 gram-force-cm/cm and, when the 141 denier monofilament yarn described above is used, the mesh has a flexibility of 14.7 gfcm/cm. In addition, depending on the yarn used to form the mesh, a mesh formed in accordance with Table I above preferably has a burst strength of about 175–250 pounds per square inch and, when the 141 denier monofilament yarn described above is used, the mesh has a mean burst strength of 223 pounds per square inch which varies between about 210 to 234 pounds per square inch depending on the sample. Finally, depending on the yarn used to form the mesh, a mesh formed in accordance with Table I above preferably has a pore size percentage of from about 37% to 50%, and, when the 141 denier monofilament yarn described above is used, the mesh has a pore size of about 42%. The polypropylene monofilament knitted mesh fabricated as described above preferably possesses a thickness of from 20 to 30 mils depending on the particular yarn used, and, when the 141 denier monofilament yarn described above is used, the mesh has a mean thickness of 24.7 mils which varies between about 24 to 25 mils depending on the sample. The flexibility, burst strength and pore size characteristics for a mesh fabric fabricated as described above and other meshes that are currently commercially available are compared in Table II set forth below:

TABLE II

| Mesh Fabric | Flexibility (gf cm/cm) | Burst Strength (PSI) | Pore Size (%) | Thickness (Mils) |
|---|---|---|---|---|
| Present Invention | 14.73 | 223 | 42.0 | 24.7 |
| Marlex Mesh (mfd. by C. R. Bard) | 14.86 | 148 | 31.71 | 25.9 |
| Prolene Mesh (mfd. by Ethicon, Inc.) | 18.92 | 241 | 49.73 | 29.0 |

As shown in Table II, the mesh of the present invention has: (i) a significantly better flexibility than the Prolene mesh fabric, and (ii) a significantly higher burst strength and pore size percentage than the Marlex mesh fabric. The mesh of the present invention thus achieves a flexibility which is slightly better than the Marlex mesh material while, at the same time, exhibiting burst strength and pore size characteristics which are comparable to the less-flexible Prolene material.

Furthermore, it is to be understood that although the present invention has been described with reference to a preferred embodiment, various modifications known to those skilled in the art, may be made to the structures and process steps presented herein without departing from the invention as recited in the several claims appended hereto.

What is claimed is:

1. A knitted surgical mesh comprised of a knitted yarn, the knitted mesh having from 11 to about 13 courses per inch and from 8 to 10 wales per inch, a flexibility of from 10 to 16 gfcm/cm, a burst strength greater than 175 pounds per square inch, and a pore size percentage greater than 37%.

2. The knitted surgical mesh of claim 1, wherein the pore size percentage of the mesh is from 37% to 50%.

3. The knitted surgical mesh of claim 2, wherein the pore size percentage of the mesh is 42%.

4. The knitted surgical mesh of claim 1, wherein the mesh has a burst strength from 210 to 234 pounds per square inch.

5. The knitted surgical mesh of claim 1, wherein the mesh has a thickness of from 20 to 30 mils.

6. The knitted surgical mesh of claim 5, wherein the thickness of the mesh is from 24 to 25 mils.

7. The surgical mesh of claim 1, wherein the yarn is a polypropylene yarn.

8. The surgical mesh of claim 7, wherein the yarn is a monofilament polypropylene yarn.

9. The surgical mesh of claim 8, wherein the yarn has a denier of from 30 to 300.

10. The surgical mesh of claim 1, wherein the mesh includes a key-hole shaped opening within an interior region of the mesh.

* * * * *